United States Patent [19]

Durette

[11] Patent Number: 5,466,259
[45] Date of Patent: Nov. 14, 1995

[54] ORBITAL IMPLANT AND METHOD

[76] Inventor: Jean-Francois Durette, 1170 East, Henri-Bourassa Blvd., Montreal, Quebec, Canada, H2C 1G4

[21] Appl. No.: 206,956

[22] Filed: Mar. 7, 1994

[51] Int. Cl.⁶ .................................................. A61F 2/14
[52] U.S. Cl. ........................................ 623/4; 623/11
[58] Field of Search ............................... 623/4, 11

[56]  References Cited

U.S. PATENT DOCUMENTS

| | | | |
|---|---|---|---|
| 2,571,721 | 1/1948 | Jardon | 623/4 |
| 2,574,750 | 10/1948 | Moore | 623/4 |
| 2,688,139 | 3/1950 | Jardon | 623/4 |
| 2,792,573 | 5/1957 | Clarke et al. | 623/4 |
| 2,810,134 | 7/1957 | Radin | 623/4 |
| 4,186,448 | 2/1980 | Brekke . | |
| 4,195,366 | 4/1980 | Jarcho et al. | 106/35 |
| 4,314,380 | 2/1982 | Miyata et al. . | |
| 4,882,148 | 11/1989 | Pinchuk | 623/4 |
| 4,950,295 | 8/1990 | Weigum et al. | 623/23 |
| 4,976,731 | 12/1990 | Perry . | |
| 5,026,392 | 6/1991 | Gordon | 623/4 |
| 5,035,713 | 7/1991 | Friis | 623/13 |
| 5,089,021 | 2/1992 | Vachet . | |
| 5,192,293 | 3/1993 | Cartwright et al. | 623/4 |
| 5,192,315 | 3/1993 | Jacob-LaBarre | 623/4 |
| 5,352,461 | 10/1994 | Feldstein et al. | 424/493 |

FOREIGN PATENT DOCUMENTS

| 4101828 | 7/1992 | Germany | 623/4 |
|---|---|---|---|

OTHER PUBLICATIONS

"Plastic Cornea" William Stone Jr. pp. 623–624.

Primary Examiner—David H. Willse
Assistant Examiner—Bruce E. Snow
Attorney, Agent, or Firm—James C. Nemmers

[57] ABSTRACT

An orbital implant is provided with a passageway extending from the anterior surface inwardly to receive a peg prior to implantation in the patient. The peg is made of non microporous material so that surrounding tissue will encapsulate the peg without adhering to it. This provides for later coupling of the ocular prosthesis to the implant without the necessity of a second operative procedure, and also allows the peg to be easily removed surgically if deemed necessary by the surgeon. The implant itself can be of any suitable material, but the implant is preferably made of biodegradable material having a matrix with random voids throughout to enhance tissue ingrowth into the implant. The matrix can be created by foaming or molding a suitable material, or the matrix can be formed from microporous thread of an inert material that is knitted, crocheted or otherwise formed into the desired size and shape.

7 Claims, 1 Drawing Sheet

ORBITAL IMPLANT AND METHOD

BACKGROUND OF THE INVENTION

The invention relates to eye replacement implants. If an eye has become damaged due to trauma or disease, the damaged eye may have to be eviscerated in which all of the inner contents of the eye are removed, or an enucleation may be performed in which the entire eyeball is removed after severing it from the eye muscles and the optic nerve. Following either of these procedures, it is common practice to fill the resulting void with an orbital implant and subsequently fit to the implant an ocular prosthesis that closely resembles the eye. When properly placed within the orbit, the orbital implant replaces the volume lost when the eye was removed and helps to maintain the normal structure of the eyelids and eyebrows. When the ocular prosthesis is properly matched to the other eye and coupled to the implant to move with it, substantially normal appearance of the patient is restored.

A variety of orbital implants have been used and are known and available, usually taking the form of a sphere or globe of suitable inert material. When the implant has been inserted following enucleation or evisceration of the eye, tissues will heal over the implant after which the ocular prosthesis is placed on the tissues that have formed over the implant. However, over a period of time, migration and extrusion of the implant can occur. In the integrated implants first used in the 1950s, the primary cause of implant migration or extrusion was that when the ocular prosthesis was coupled to the orbital implant, it was necessary to expose a portion of the implant to the outside environment, thereby allowing bacteria to enter and infect the implant. Another cause of implant migration and extrusion is the lack of tissue supposedly covering the implant thereby allowing possible infection to enter through any opening where the implant is not covered by tissue. Also, sometimes the tissues which have previously covered the implant become pressured and necrose, thus allowing bacteria to enter and cause infection. This can occur years after the implant is made.

A number of attempts have been made to overcome these and other problems of implant migration and extrusion. Perry, U.S. Pat. No. 4,976,731 teaches the use of an orbital implant made of low density hydroxyapatite, and following implantation of the implant and during the healing process, tissue penetrates the porous structure of the implant as the scleral sac or other covering is absorbed into the system. Perry teaches that after sufficient healing has occurred, the implant can be drilled to provide a passageway that allows the ocular prosthesis to be attached to the implant by insertion of a peg protruding from and forming a part of the prosthesis. Perry asserts that this will resolve the concern of migration or extrusion of the implant because tissue will also grow into and provide a lining for the drilled passageway. However, even using the Perry recommended material for the implant, a second surgical procedure is required with the normal risks of such procedures, including infection of the tissue around the peg implant.

Vachet, U.S. Pat. No. 5,089,021, teaches the use of a spherical core over which there is bonded a layer of material made from a micro-porous, bio-compatible synthetic substance such as polytetrafluorethylene (EPTFE). Vachet claims that with this implant construction, the coating layer will be invaded by fibroblasts and blood vessels which will gradually transfer the coating layer into a tissue and vascular shell and thus minimize the risk of migration and extrusion of the implant. Vachet then asserts that following healing, the patient can be fitted with an ocular prosthesis by carefully molding the prosthesis over the tissues covering the implant. However, since the only traction between the prosthesis and the implant is from the tissues forming the posterior aspect of the socket, this technique may produce less than satisfactory motility.

In all of the prior art teachings, references are made to the use of a variety of different materials for the orbital implant which materials are all preferably inert. Also, the prior art teaches the use of materials which are microporous so that the surrounding tissue will eventually penetrate the implant to hold it in place and thereby minimize the possibility of extrusion of the implant. Perry, U.S. Pat. No. 4,976,731, referred to above is an example of this teaching. The prior art also teaches the use of different synthetic materials that are used by oral and orthopedic surgeons to replace voids created in bone structures. Brekke U.S. Pat. No. 4,186,448 is an example of such a teaching in which bone voids created by fracture, surgery, etc. are treated by filling the voids with a material that is bio-degradable and which has randomly positioned voids throughout substantially all of the its volume. Brekke also teaches the use of a wetting agent incorporated in the material to promote the filling of the voids in the material with blood vessels so as to form tissue that will fill the voids. Eventually, this material becomes absorbed.

However, prior art materials that are currently known and used for some eye implants are quite expensive, and those that are not microporous, occasionally require additional surgical procedures to minimize migration and extrusion. In addition, the known structures and techniques for integrating the ocular prosthesis with the orbital implant are not entirely satisfactory. Some such techniques require post-surgical drilling of the implant after healing has occurred adding to the cost and patient trauma and always with risk of infection.

There is therefore a need for an improved orbital implant that will reduce the surgical procedures and time involved and thus lower the cost of the overall implant process as well as provide for improved integration of the implant with the ocular prosthesis. There is furthermore a need for the use of improved materials for the orbital implant which materials will reduce greatly the likelihood of migration or extrusion of the implant.

SUMMARY OF THE INVENTION

One aspect of the invention provides an orbital implant of any suitable material which is pre-drilled or pre-formed with a passageway extending inwardly from the anterior surface for receipt of an implant peg of a non-microporous material. The orbital implant with the peg in place is then surgically inserted following either enucleation or evisceration. Since the peg is of a non-microporous material, a fibrous capsule will form around it but not adhere to it, which allows the surgeon to later remove the peg implant easily from the orbital implant if deemed necessary. Moreover, the peg implant provides a means for direct integration with the ocular prosthesis for improved motility.

Another aspect of the invention provides for the use of microporous threads formed into a sphere by knitting, crocheting or any other procedure so as to form an orbital implant of the desired size and shape containing a plurality of continuous voids to facilitate tissue invasion. A further aspect of the use of microporous threads is to form the orbital implant into a sphere using any suitable material and then cover either the anterior surface only or the entire surface of the sphere with a thin sheet of soft material formed of a microporous material. Materials suitable for this aspect of the invention are polyproplyene, polyesthers (Mercilene, Dacron) and ePTFE, which is expanded polytetrafluoroethylene.

Another aspect of the invention is to form the orbital implant from an absorbable, bio-degradable material such as polylactic acid (PLLA), polyglycolic acid (PLA) or absorbable coral or any other absorbable material.

Regardless of the use of the particular material for the orbital implant, the implant may be pre-drilled or pre-formed to receive a peg of non-microporous material. The anterior surface of the ball peg or flat peg could be lined, if desired, with a microporous inert biomaterial such as ePTFE, etc. The ingrowth of tissue that occurs will decrease the possibility of exposure of the peg and prevent having to remove the peg to replace it.

DESCRIPTION OF THE PREFERRED EMBODIMENTS OF THE INVENTION

Figure 1:
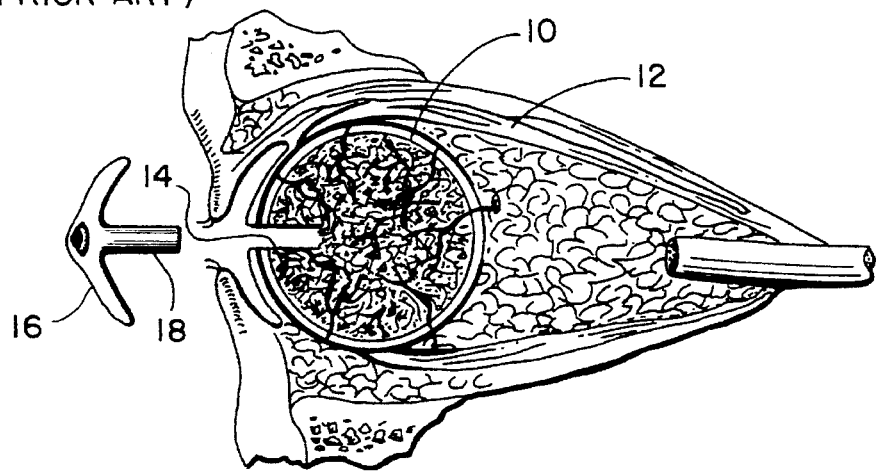
FIG. 1 is a sectional view illustrating the existing art regarding the use of orbital implants integrated with an ocular prosthesis.
Figure 2:
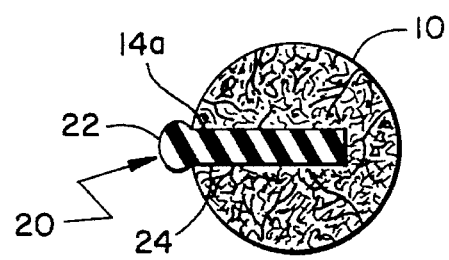
FIG. 2 is a sectional view of an orbital implant illustrating one aspect of the invention in which the peg is integrated with the orbital implant by insertion in a pre-formed opening.

FIG. 1 illustrates a known implant and technique in which the orbital implant 10 is in place and attached to the eye muscles 12 to provide for motility. The implant 10 has a longitudinal passageway formed in it extending inwardly from its anterior surface. The present teaching is that the passageway 14 is drilled into the implant after the implantation procedure has been completed and after a period of healing of a few months. At this time, the ocular prosthesis 16 that is formed with an integral peg 18 is attached to the implant 10 by insertion of the peg 18 into the passageway 14 of the implant 10. However, if bacteria enter the space between the tissue and the peg 18, or if the implant 10 is not ingrown, exposure of the implant 10 may occur. The infection results from exposure of the implant 10 to the outside environment after the drilling procedure necessary to attach the ocular prosthesis 16.

Figure 3:
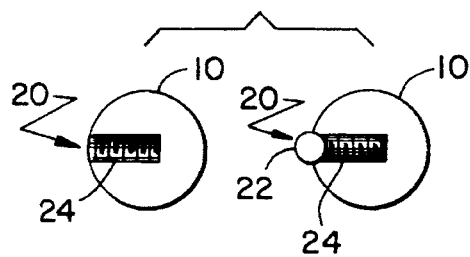
FIG. 3 illustrates the use of either a flat peg or a ball peg.
Figure 4:
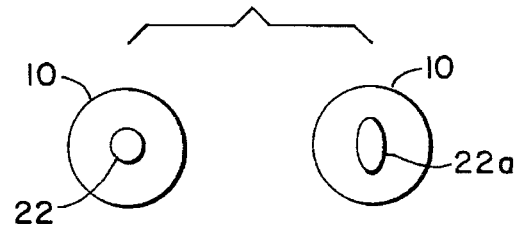
FIG. 4 is a front view of the implant to illustrate the use pegs which are circular in cross-section or which have a ball that is elongated in one dimension.

In the first aspect of the invention, the orbital implant 10 is formed with a passageway 14a in it. The passageway 14a extends from the interior surface of the implant 10 inwardly along a radial line, and is either formed at the time the implant 10 is produced, such as by molding, or the passageway 14a can be drilled into the implant 10 prior to sterilization and implantation. Also prior to sterilization and implantation, the implant 10 is provided with a peg 20 of a non-microporous material such as an elastomeric material like silicone. The peg 20 is formed in the shape of a flat peg with no head or a ball peg having a head 22. The head 22 may be spherical as illustrated in FIG. 4 or it may be elongated in one direction as illustrated by the head 22a also shown in FIG. 4 which is a front view of the orbital implant 10. The main body 24 of the peg 20 may be provided with a ridge or screw as illustrated in FIG. 3 to allow tissue to fill the voids and prevent the peg 20 from moving freely in the passageway 14a.

Since the peg 20 is formed of a non-microporous material, once the implant 10 containing the peg 20 is implanted in tissue, a fibrous capsule will form around the peg 20, and the capsule will not adhere to the elastomeric material. This allows the surgeon to later remove the peg 20 from the implant 10 if deemed necessary. If the peg 20 is made of elastomeric material, it will stretch and can be easily extracted.

The use of the ball peg 22 provides for direct integration of the implant 10 with any suitable ocular prosthesis. If the elongated ball 22a is utilized, undesirable rotation of the ocular prosthesis will be decreased. Of course, if the flat peg 20 is used, there will be no direct integration with the prosthesis, and if improved motility is desired at a later date, a small portion of the conjunctiva and the tenon can be incised allowing extraction of the flat peg 20 and insertion of any other peg including the commonly known and used sleeved peg.

By pre-forming the passageway 14a in the orbital implant 10, the secondary procedure for drilling the implant 10, after implantation and healing, is eliminated. If after implantation the ball peg 20 of the invention should become exposed due to pressure necrosis, for example, it will always be possible to extract the peg 20 and replace it with the commonly known and used sleeved peg. However, the anterior surface of the ball peg or flat peg can be lined, if desired, with a microporous inert biomaterial such as ePTFE, etc. The ingrowth of tissue that occurs will decrease the possibility of exposure of the peg and prevent having to remove the peg to replace it.

The peg 20 can be made of any suitable type of material which generates encapsulation and to which tissues will not readily adhere. The material for the implant 10 can also be of any suitable known material, since any of the materials suitable for the orbital implant 10 can be easily formed with the passageway 14a. Suitable materials include nylon, polyvinylfluoridene, etc. However, another aspect of the invention is to produce the implant 10 from a microporous or braided thread of a suitable material such as polyproplyene, polyester (Mercilene, Dacron) or expanded polytetrafluoroethylene (ePTFE). These materials are suitable because of their inertness in the body as well as being microporous and therefore providing some tissue invasion after the implantation procedure. The braided or monofilament threads are formed into the desired spherical shape, and when so formed, the implant 10 will contain a plurality of voids or matrix that will encourage tissue ingrowth and decrease the possibility of migration.

In another aspect of the invention, the implant 10 can be produced of any suitable material, including the braided thread construction, and then covered either partially or fully with a sheet of microporous material such as polyproplyene, polyester (Mercilene, Dacron), expanded PTFE (Teflon), etc. If a partial covering is made, only the anterior surface of the implant 10 is covered, with the covering either sutured or attached to the implant in with a suitable adhesive.

In another aspect of the invention, the implant 10 can be formed using an absorbable, bio-material. Examples of such material are foamed polylactic acid (PLLA) or polyglycolic acid (PGA). Foam structures of these materials produce a matrix containing a plurality of continuous voids. Initially, the implant 10 fills the void created due to enucleation or evisceration. During the healing period following the surgical procedure, cellular ingrowth and fibro vascularization will attach to all the surrounding tissues and create a fibrous capsule to which the muscles previously sutured to the implant 10 will remain attached. After a period of months and after the healing process has slowed or stopped, the matrix of the implant will have entirely absorbed and the space previously occupied by the implant 10 will be filled by more tissue ingrowth. If a matrix of foamed polylactic acid is used, the material comprises only five percent of the total volume, the remaining being the air space of the voids. As the material is absorbed over time, some shrinkage may occur in the implant but this should be negligible. Since the matrix structure of the implant 10 is random, the fibrous tissue will grow in almost every direction to minimize contracture. Moreover, these new tissues can then be surgically altered as needed to practically eliminate the possibility of late migration or malposition. Extrusion will not occur after the material is absorbed. For example, if more orbital volume is needed, another implant of the desired size and shape can be implanted within these soft fibrous tissues. Also, if the posterior aspects of the ocular socket are unacceptable and cause a problem in fitting the ocular prosthesis, some of the soft tissues can be surgically altered with relative ease. Thus, the use of an absorbable material has tremendous potential for improved patient care.

Use of a polylactic acid structure for the implant 10 also provides for attachment of the muscles by suturing, and the implant need not be wrapped or encased with any material. This eliminates the commonly used surgical technique of wrapping implants in sclera or fascia.

In another aspect of the invention, caps formed of foamed polylactic acid can be placed in front of a spherical shaped implant 10. These curved caps are of a preferred thickness of 1 to 2 mm and during the implant procedure are positioned over the spherical implant before closing tenon's and conjunctiva. In this aspect of the invention, the space occupied by the foamed cap offers a matrix that will be invaded first by fibroblasts and then by vascular ingrowth. Over a period of time, this matrix will create an extra layer of tissue over the implant 10 and under tenon's and conjunctiva. This new tissue created on the anterior surface of the implant 10 will serve as a cushion between the implant 10 and the ocular prosthesis.

From the foregoing description, it will be evident that the various aspects of the invention provide new and improved techniques for eye replacement implants. With the use of the materials described herein for the basic implant or for coverings for implants, and in selected cases preforming the implant with a passageway for receipt of a peg prior to implantation, the surgeon has available a number of new and improved materials and techniques that can be used in any particular case depending upon the judgment of the surgeon. By providing the surgeon with new and improved options, the eye replacement procedures can be performed at lower cost and with less trauma to the patient.

Having thus described the invention in connection with certain preferred embodiments and aspects thereof, it will be evident to those skilled in the art that various provisions and modifications can be made to the preferred embodiments described herein without departing from the spirit and scope of the invention. It is my intention, however, that all such revisions and modifications that are obvious to those skilled in the art will be included in the scope of the following claims.

What is claimed is as follows:

1. An orbital implant for coupling with an ocular prosthesis to replace an eye following evisceration or enucleation, said implant comprising a sphere having an anterior surface and a posterior surface when implanted, the sphere being formed of braided threads of a microporous material that provide a plurality of voids for tissue ingrowth.

2. The orbital implant of claim 1 in which the sphere is combined with a sheet of microporous material.

3. The orbital implant of claim 2 in which the entire sphere is covered with the sheet of microporous material.

4. The orbital implant of claim 2 in which only the anterior surface is covered with the sheet of microporous material.

5. An orbital implant for coupling with an ocular prosthesis to replace an eye in a patient following evisceration or enucleation, said implant comprising a sphere sized to replace the volume of the eye and having an anterior surface and a posterior surface when implanted, the sphere being made of an absorbable bio-material forming a matrix having a plurality of continuous random voids that promote ingrowth of surrounding tissue after the implant is in place in the patient, the absorbable bio-material being foamed polylactic acid.

6. An orbital implant for coupling with an ocular prosthesis to replace an eye in a patient following evisceration or enucleation, said implant comprising a sphere sized to replace the volume of the eye and having an anterior surface and a posterior surface when implanted, the sphere being made of an absorbable bio-material forming a matrix having a plurality of continuous random voids that promote ingrowth of surrounding tissue after the implant is in place in the patient, the absorbable bio-material being foamed polyglycolic acid.

7. An orbital implant for coupling with an ocular prosthesis to replace an eye in a patient following evisceration or enucleation, said implant comprising a sphere sized to replace the volume of the eye and having an anterior surface and a posterior surface when implanted, the sphere being made of an absorbable bio-material forming a matrix having a plurality of continuous random voids that promote ingrowth of surrounding tissue after the implant is in place in the patient, the absorbable bio-material being absorbable coral.

\* \* \* \* \*